(12) United States Patent
Chen et al.

(10) Patent No.: US 8,735,176 B2
(45) Date of Patent: May 27, 2014

(54) METAL OXIDE NANO-COMPOSITE MAGNETIC MATERIAL, FABRICATION METHOD, AND METHOD FOR LINKAGE, ENRICHMENT, AND ISOLATION OF PHOSPHORYLATED SPECIES

(75) Inventors: Yu-Chie Chen, Hsinchu (TW); Cheng-Tai Chen, Taoyuan County (TW); Wei-Yu Chen, Taipei (TW); Chun-Yuen Lo, Kaohsiung (TW); Hong-Yi Lin, Taoyuan County (TW); Chih-Chi Liu, Chiayi (TW)

(73) Assignee: National Chiao Tung University, Hsinchu (TW)

( * ) Notice: Subject to any disclaimer, the term of this patent is extended or adjusted under 35 U.S.C. 154(b) by 888 days.

(21) Appl. No.: 12/101,451

(22) Filed: Apr. 11, 2008

(65) Prior Publication Data
US 2009/0050839 A1 Feb. 26, 2009

Related U.S. Application Data

(60) Provisional application No. 60/940,505, filed on May 29, 2007.

(51) Int. Cl.
*G01N 33/552* (2006.01)
*G01N 33/551* (2006.01)

(52) U.S. Cl.
CPC ............ *G01N 33/552* (2013.01); *G01N 33/551* (2013.01)
USPC ............................ 436/527; 436/524; 436/525

(58) Field of Classification Search
None
See application file for complete search history.

(56) References Cited

U.S. PATENT DOCUMENTS

2006/0246225 A1* 11/2006 Moritz et al. ............... 427/376.2
2007/0117224 A1* 5/2007 Croker et al. ................ 436/527

OTHER PUBLICATIONS

Graf et al. "A General Method to Coat Colloidal Particles with Silica". Langmuir. 2003. vol. 19, pp. 6693-6700.*
Philip Cohen; The Origins of Protein Phosphorylation; Nature Cell Biology; vol. 4, May 2002; 2002 Nature Publishing Group; pp. E127-E130.
Scott B. Ficarro, Mark L. Mccleland, P. Todd Stukenberg, Daniel J. Burke, Mark M. Ross, Jeffrey Shabanowitz, Donald F. Hunt, and Forest M. White, Phosphoproteome Analysis by Mass Spectrometry and Its Application to *Saccharomyces cerevisiae*; http://biotech.nature.com; Mar. 2002, vol. 20, Nature Biotechnology, pp. 301-305.

(Continued)

*Primary Examiner* — Robert Xu
(74) *Attorney, Agent, or Firm* — Rosenberg, Klein & Lee (57) ABSTRACT

The present invention relates to a metal oxide nano-composite magnetic material, fabrication method, and method for linkage, enrichment, and isolation of phosphorylated species. The metal oxide nano-composite magnetic material comprises the magnetic iron oxide nanoparticle, a silica layer immobilized onto the magnetic iron oxide nanoparticle and a metal oxide layer coated onto the silica layer. The magnetic iron oxide nanoparticles can be used for absorbing microwave radiation to accelerate the enrichment and linkage for phosphorylated species onto the metal oxide nano-composite magnetic material. Furthermore, the magnetic property of magnetic iron oxide nanoparticles leads to isolation of the metal oxide nano-composite magnetic material-target species conjugates by simply employing an external magnetic field. The specificity of the metal oxide on the surface of the metal oxide nano-composite magnetic material for phosphorylated species also leads to the linkage/enrichment of phosphorylated species with high selectivity.

1 Claim, 11 Drawing Sheets

(56) References Cited

OTHER PUBLICATIONS

Thomas Kocher, Gunter Allmaier, and Matthias Wilm, Nanoelectrospray-based Detection and Sequencing of Substoichiometric Amounts of Phosphopeptides in Complex Mixtures, Journal of Mass Spectrometry, published online Jan. 9, 2003 in Wiley InterScience (www.interscience.wiley.com), pp. 131-137.

Florian Wolschin, Stefanie Wienkoop and Wolfram Weckwerth, Enrichment of Phosphorylated Proteins and Peptides from Complex Mixtures Using Metal Oxide/Hydroxide Affinity Chromatography (MOAC); Proteomics 2005, 2005 Wiley-VCH Verlag GmbH & Co. KGaA, Weinheim, pp. 4389-4397.

Greg T. Cantin, Teresa R. Shock, Sung Kyu Park, Hiten D. Madhani, and John R. Yates III, Optimizing TiO2-Based Phosphopeptide Enrichment for Automated Multidimensional Liquidimensional Liquid Chromatography Coupled to Tandem Mass Spectrometry; Analytical Chemistry, vol. 79, No. 12, Jun. 15, 2007, pp. 4666-4673.

Naoyuku Sugiyama, Takeshi Masuda, Kosaku Shinoda, Akihiro Nakamura, Masaru Tomita, and Yasushi Ishihama, Phosphopeptide Enrichment by Aliphatic Hydroxy Acid-modified Metal Oxide Chromatography for Nano-LC-MS/MS in Proteomics Applications; Molecular & Cellular Proteomics 6.6; http://www.mcponline.org; pp. 1103-1109.

Cheng-Tai Chen and Yu-Chie Chen; FE304/TiO2 Core/Shell Nanoparticles As Affinity Probes for the Analysis of Phosphopeptides Using TiO2 Surface-Assisted Laser Desorption/Ionization Mass Spectrometry; Analytical Chemistry, vol. 77, No. 18, Sep. 15, 2005, pp. 5912-5919.

Chun-Yuen Lo, Wei-Yu Chen, Cheng-Tai Chen, and Yu-Chie Chen; Rapid Enrichment of Phosphopeptides from Tryptic Digests of Proteins Using Iron Oxide Nanocomposites of Magnetic Particles Coated with Zirconia as the Concentrating Probes, Journal of Proteome Research 2007, 6, pp. 887-893.

J.W. Walkiewicz, G. Kazonich, and S.L. McGill, Microwave Heating Characteristics of Selected Minerals and Compounds, Minerals and Metallurgical Processing, Feb. 1988, pp. 39-42.

Wei-Yu Chen and Yu-Chie Chen, Maldi MS Analysis of Oligonucleotides: Desalting by Functional Magnetite Beads Using Microwave-Assisted Extraction, Analytical Chemistry, vol. 79, No. 21, Nov. 1, 2007, pp. 8061-8066.

\* cited by examiner

METAL OXIDE NANO-COMPOSITE MAGNETIC MATERIAL, FABRICATION METHOD, AND METHOD FOR LINKAGE, ENRICHMENT, AND ISOLATION OF PHOSPHORYLATED SPECIES

REFERENCE TO RELATED APPLICATION

This Application is based on Provisional Application Ser. No. 60/940,505, filed 29 May 2007, currently pending.

BACKGROUND OF THE INVENTION

1. Field of the Invention

The invention displays the fabrication method for a metal oxide nano-composite magnetic material and their uses in linkage, enrichment, and isolation of phosphorylated species. Furthermore, this invention especially addresses the applications for the enrichment and isolation of phosphorylated peptide/proteins from complex samples by using the proposed metal oxide nano-composite magnetic nanoparticles as affinity probes.

2. Description of Related Art

Protein phosphorylation is one of the most common protein post-translational modifications. Phosphorylated proteins play an important role for signal transduction and cell regulation in biological systems. Nevertheless, the abundance of phosphorylated proteins is generally low in biological samples (Cohen, P., *Nature Cell Biology* 4, E127-E130 (2002)). Therefore, it is necessary to develop suitable methods for selectively enriching traces of phosphorylated proteins from complex samples. Hence, many technologies for purifying phosphorylated proteins and phosphorylated peptides have been developed. Among these technologies, immobilized metal ion chromatography (IMAC), which immobilizes $Fe^{3+}$ and $Ga^{3+}$ onto solid substrates, has been used for purification of phosphorylated species from complex samples by Ficarro, S. B. et al., *Nature Biotechnology* 19, 301-305 (2002). The phosphorylated species can strongly interact with metal ions on the IMAC substrate.

Although IMAC has been widely used for purifications of phosphorylated proteins/peptides, there are some problems arising in IMAC. For example, non-specific binding, which may result in low sensitivity and poor extraction capacity, remains a problem in IMAC that has been investigated by Thomas, K. et al., *J. Mass Spectrom.* 38, 131-137 (2003). Metal oxide affinity chromatography (MOAC) is an alternative approach used for selectively enriching phosphorylated proteins/peptides based on the interaction between metal oxides and phosphates (Wolschin, F. et al., *Proteomics* 5, 4389-4397 (2005)). Conventionally, chromatographic columns packed with metal oxide coated beads are used for the enrichment of phosphorylated species. Columns packed with titanium oxide and zirconium oxide have been employed in MOAC for enriching phosphorylated peptides/proteins by Cantin, G. T. et al., *Anal. Chem.* 79, 4666-4673 (2007); Sugiyama N. et al., *Mol. Cell Proteomics* 6, 1103-1109 (2007). For ease of use, we have previously demonstrated that titanium oxide/zirconium coated magnetic nanoparticles can be used as effective affinity probes for phosphopeptides/proteins (Chen, C. T. and Chen, Y. C. *Anal. Chem.* 77, 5912-5919 (2005); Lo, C. Y.; Chen, W. Y.; Chen, C. T. and Chen, Y. C. *J. Proteome Res.* 6, 887-893 (2007)). This approach greatly simplifies the steps for isolation of probe target species from sample solutions because probe-target species conjugates can easily be isolated by magnetic separation. Moreover, the problem of non-specific binding is greatly reduced. We further explore several types of metal oxide coated magnetic nanoparticles (MOMNPs), which is the invention presented herein. In addition, microwave heating is utilized in accelerating the enrichment of phosphorylated proteins/peptides by MOMNPs because magnetic nanoparticles (MNPs) are good microwave absorbers, first investigated by Walkeiwicz, J. W. et al., *Miner. Metall. Proc.* 124, 247-252 (1988). Chen, W. Y. and Chen, Y. C. *Anal. Chem.* 79, 8061-8066 (2007), have previously demonstrated that extraction of traces of oligonucleotides from a sample solution could be completed using MNPs as the adsorbents under microwave heating within 30 sec. This invention also combines this technique to this MOMNPs approach. It has been demonstrated that metal oxide nano-composite magnetic material can be used to selectively enrich traces of phosphorylated species from complex samples within 30~90 sec and then the target species of metal oxide nano-composite magnetic material can be characterized by matrix-assisted laser desorption/ionization mass spectrometry (MALDI MS). Thus, the advantages of the present invention involve short analysis time, high specificity, and high sensitivity.

BRIEF SUMMARY OF THE INVENTION

The present invention relates to a method by employing metal oxide nano-composite magnetic materials for linkage, enrichment, and isolation of phosphorylated species. That is, phosphorylated species such as phosphopeptides and phosphoproteins can be selectively trapped on the surface of the metal oxide nano-composite magnetic material. Functional molecules, which have the capability of targeting specific species, with phosphate functional groups can be readily linked with the metal oxide nano-composite magnetic material via chelating by simply mixing them together. Furthermore, this present invention provides an extremely simple method for fabrication of functional magnetic nanoparticles. That is, the metal oxide nano-composite magnetic material accelerating microwave-assisted linkage/enrichment of phosphorylated species, which only requires 30~90 sec, is demonstrated in this invention. Moreover, based on the magnetic property of the metal oxide nano-composite magnetic material, the metal oxide nano-composite magnetic material-target species can be rapidly isolated from sample solutions by employing a magnetic field. Thus, the main advantage of this present invention is its high selectivity and speed.

BRIEF DESCRIPTION OF THE DRAWINGS

In the drawings forming a part of this disclosure.

DETAILED DESCRIPTION OF THE PREFERRED EMBODIMENT

The present invention is susceptible to embodiment in various forms as shown in the drawings. However, a preferred embodiment will be described with the understanding that the present disclosure is to be considered an exemplification of the invention and is not intended to limit the invention of the specific embodiments illustrated.

Figure 1:
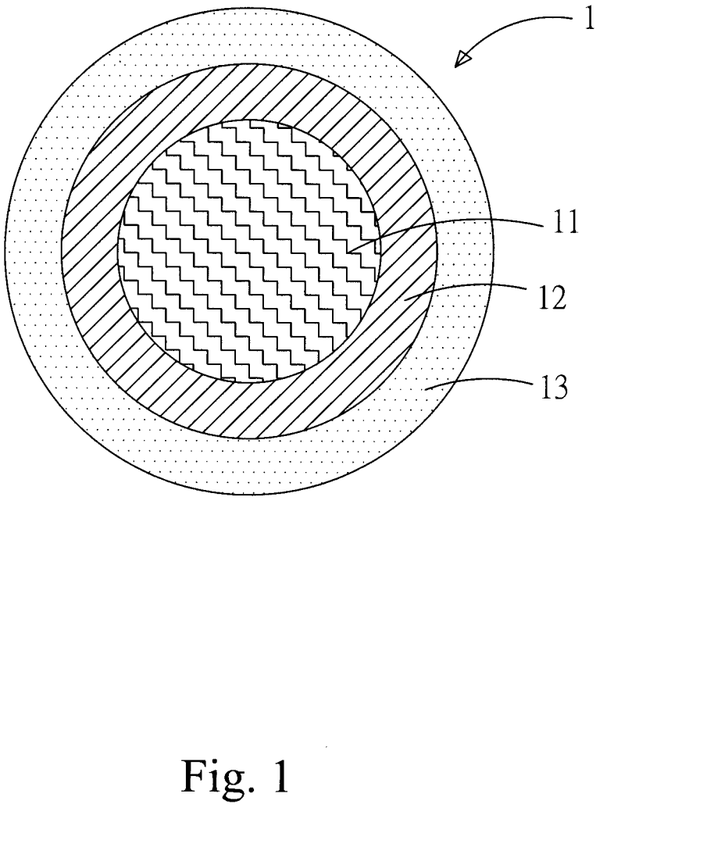
FIG. 1 depicts the schematic of the metal oxide nano-composite magnetic material in the present invention.
Figure 2:
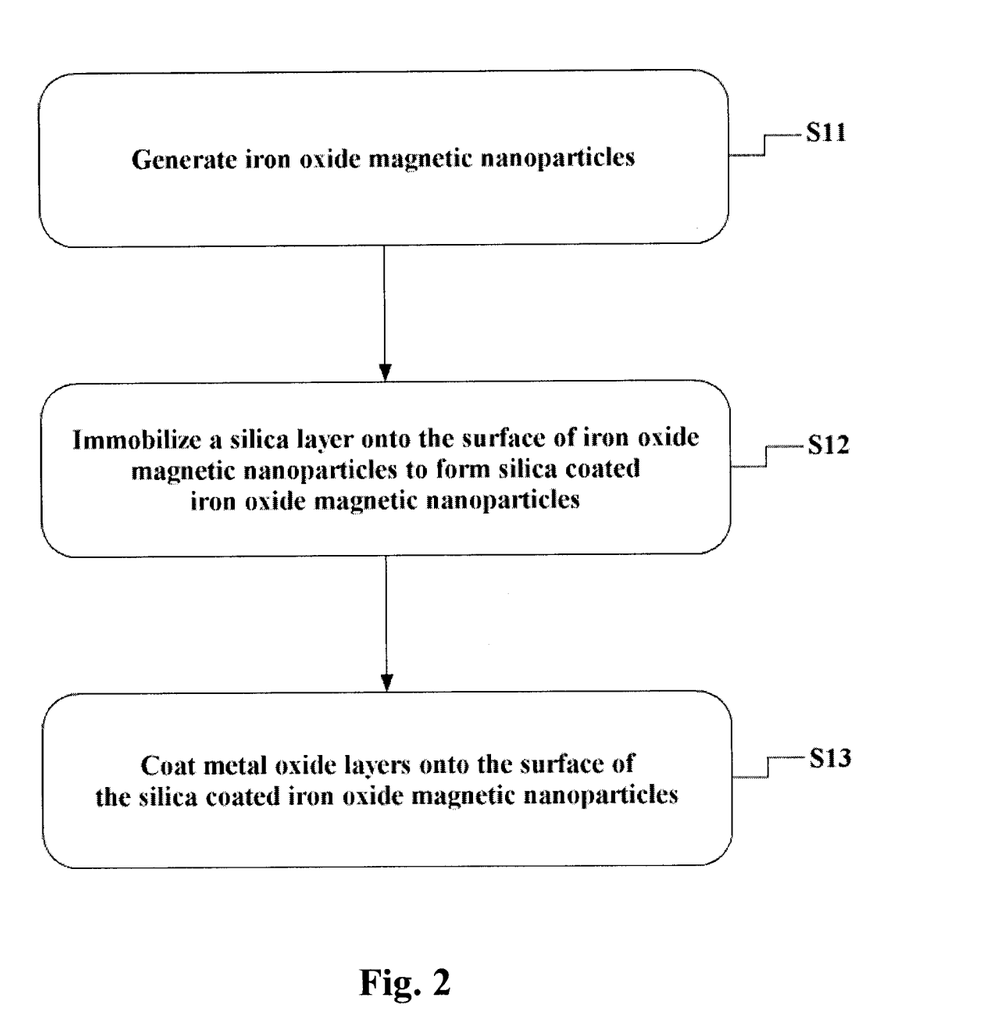
FIG. 2 is the flow chart for the fabrication of metal oxide nano-composite magnetic material in the present invention.
Figure 3:
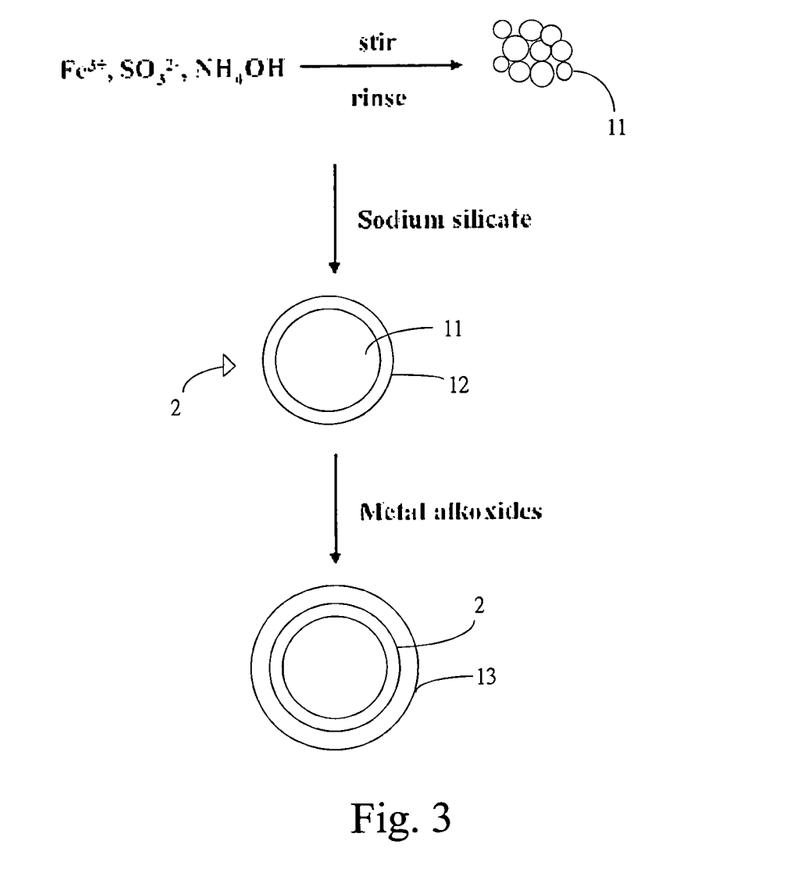
FIG. 3 is the diagram for the fabrication of metal oxide nano-composite magnetic material in the present invention.

Referring to FIG. 1, the metal oxide nano-composite magnetic material 1 of the present invention comprises of a magnetic iron oxide nanoparticle 11, a silica layer 12 immobilized onto the surface of the magnetic iron oxide nanoparticle 11, and a metal oxide layer 13 coated onto the surface of the silica layer 12. The material of the metal oxide layer is selected from consisting of aluminum oxide, niobium oxide and zinc oxide. Referring to FIG. 2 and FIG. 3, the method for fabrication of the present invention's metal oxide nano-composite magnetic material comprises the following steps:

S11 generating magnetic iron oxide nanoparticles 11.
S12 immobilizing a silica layer 12 onto the magnetic iron oxide nanoparticle 11 to form a silica coated magnetic iron oxide nanoparticle 2.
S13 coating at least one metal oxide layers 13 onto the surface of the silica coated magnetic iron oxide nanoparticle 13.

The step S11 is carried out by reacting iron chloride with aqueous sodium sulfite in hydrochloric acid solution or by mixing $FeCl_3$ and $FeCl_2$ in aqueous hydrochloric acid, followed by reacting with ammonia.

The step S12 is performed by reacting sodium silicate with the magnetic iron oxide nanoparticle or by reacting tetraethoxysilane and ammonia with the magnetic iron oxide nanoparticle.

The step S13 is carried out by reacting the silica coated magnetic iron oxide nanoparticle with aluminum isopropoxide to generate a metal oxide nano-composite magnetic material or by reacting niobium oxide sol-gel with the silica coated magnetic nanoparticle. The step of generating niobium oxide sol-gel is carried out by reacting niobium ethoxide in the solvent of ethanol and acetylacetone, followed by the addition of acetic acid.

Figure 4:
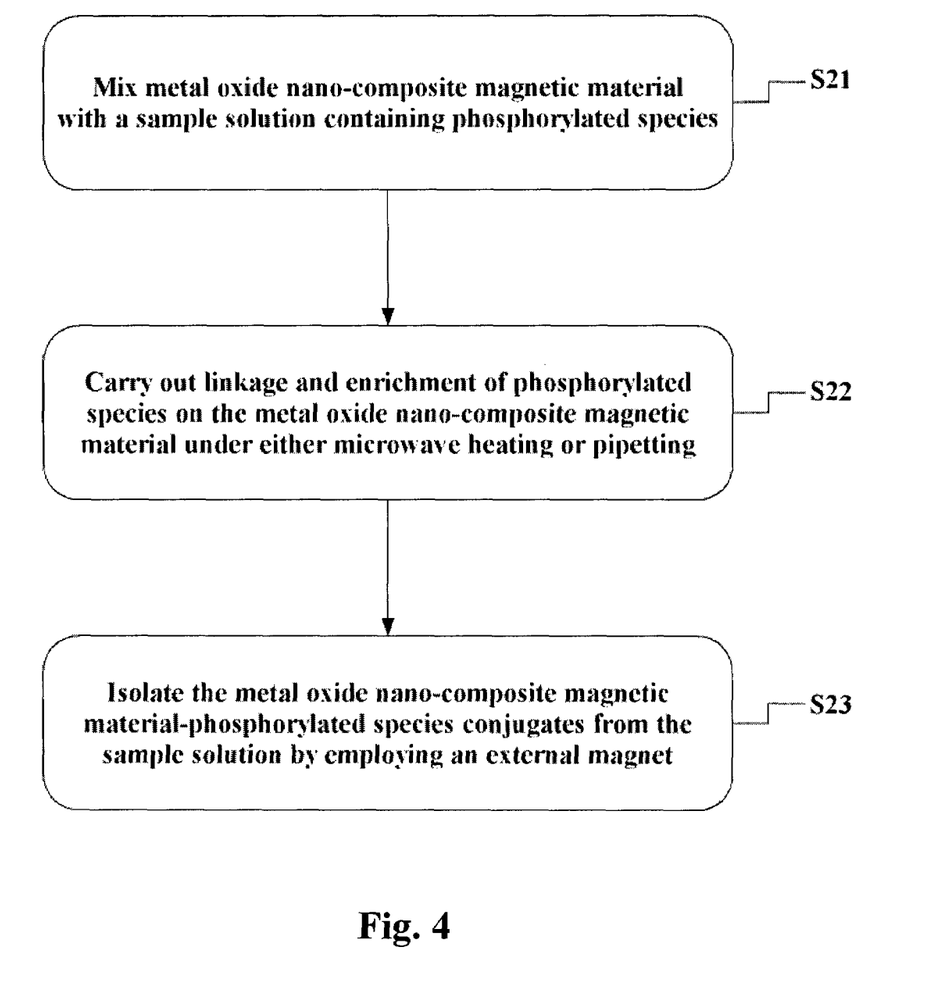
FIG. 4 is the flow chart for linking, enriching, and isolating phosphorylated species from sample solutions onto metal oxide nano-composite magnetic material in the present invention.
Figure 5:
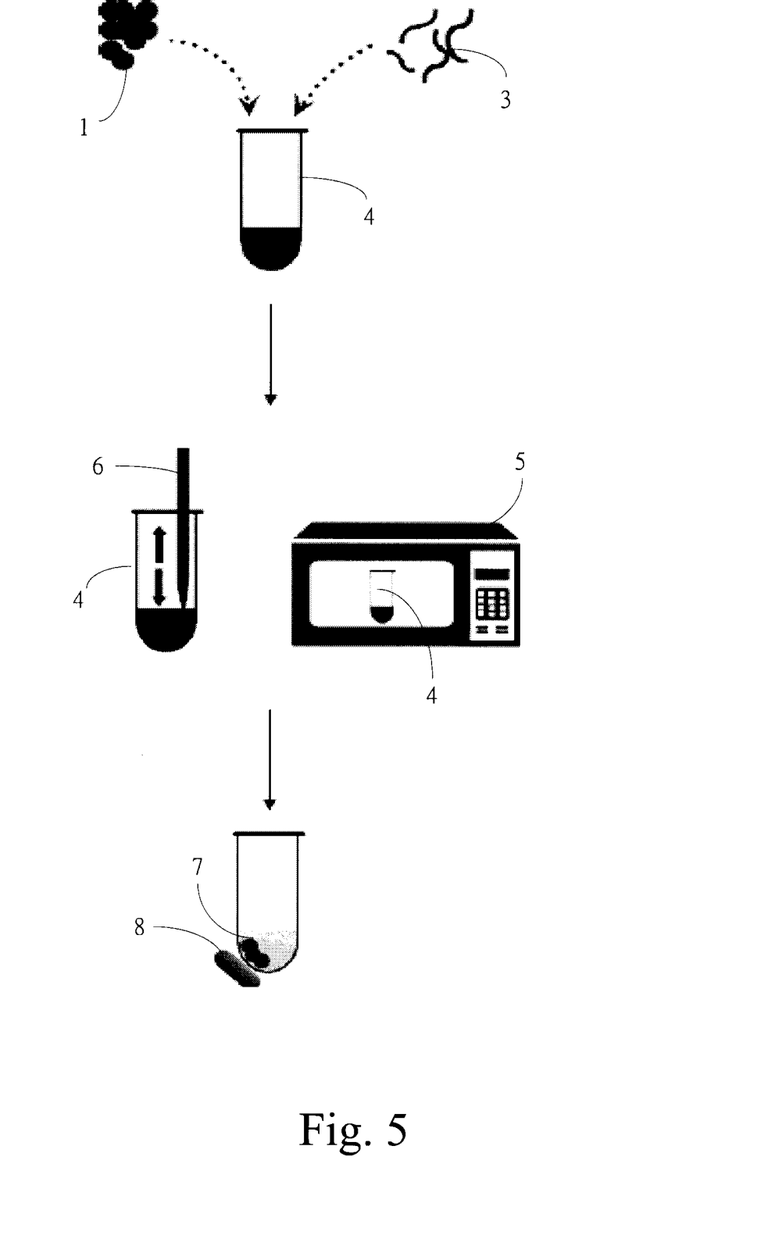
FIG. 5 is the diagram for linking, enriching, and isolating phosphorylated species from sample solutions onto metal oxide nano-composite magnetic material in the present invention.

Referring to FIG. 4 and FIG. 5, the method for linkage, enrichment, and isolation of phosphorylated species of the present invention comprises the following steps:

S21 mixing metal oxide nano-composite magnetic material 1 with sample solutions containing phosphorylated 3 species in a vial 4.
S22 carrying out linkage and enrichment of phosphorylated species on the metal oxide nano-composite magnetic material under either microwave heating (by a microwave oven 5) or pipetting (by a pipet 6).
S23 isolating the metal oxide nano-composite magnetic material-phosphorylated species conjugates 7 from the sample solution by employing an external magnet 8.

The step S21 is carried out in aqueous trifluoroacetic acid.
In the step S22, microwave heating time is 30~90 seconds. Also, the step S22 is based on the chelating capability of phosphates on the phosphorylated species and the metal on metal oxides such as aluminum and niobium on the metal oxide nano-composite magnetic material.

After the step S23, further comprises a step of confirming the phosphorylated species enriched by the metal oxide nano-composite magnetic material is carried out by MALDI MS.

First Preferred Embodiment

Methods for Generating Metal Oxide Nano-Composite Magnetic Materials magnetic iron oxide nanoparticles were prepared by the steps described as follows. Iron(III) chloride ($FeCl_3 \cdot 6H_2O$, 6.48 g) was dissolved in hydrochloric acid (2 M, 12 mL) and then diluted in 100 mL of water. The mixture was degassed using a pump. Sodium sulfite (50 mL, 0.08 M) was slowly added to the solution under nitrogen with stirring at room temperature. Subsequently, ammonia (5%, 45 mL) was added slowly to the reaction solution with vigorously stirring at room temperature. The whole mixture was left to react for 30 min in a water bath at 70° C. The magnetic iron oxide nanoparticles were rinsed with deionized water three times.

Figure 6:
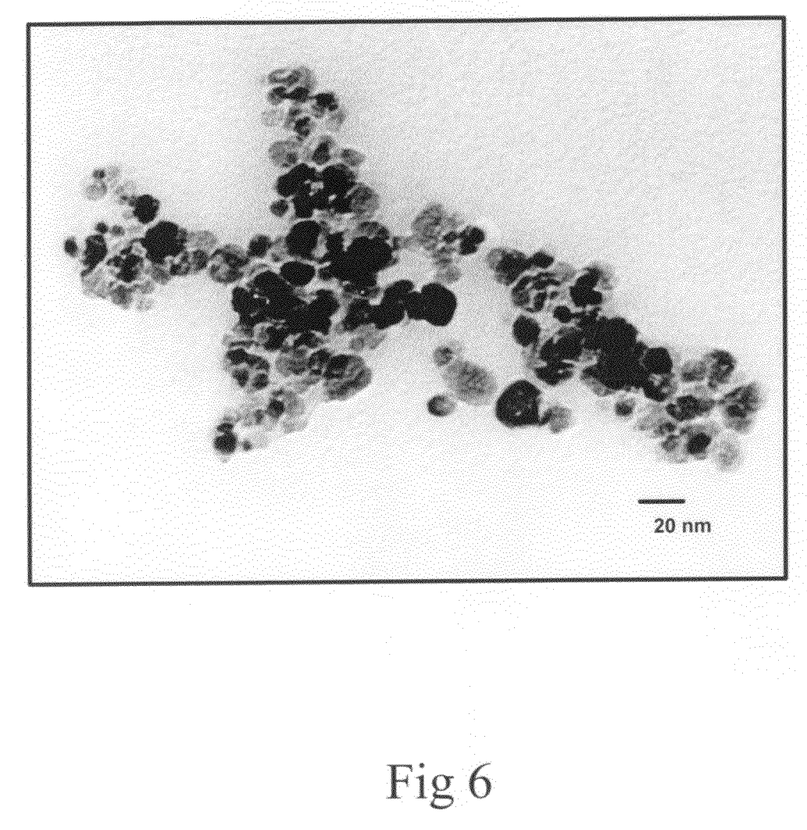
FIG. 6 presents the SEM image of aluminum oxide nano-composite magnetic nanoparticles in the present invention's first preferred embodiment.

The magnetic iron oxide nanoparticles in water (5 mg/mL, 40 mL) was well suspended in an air-free condition by sonication under nitrogen gas. Sodium silicate aqueous solution (0.6%, pH 9, 40 mL) was added into the solution and was vortex-mixed for 24 h at 35° C. to coat a thin film of $SiO_2$ onto the surfaces of the magnetic iron oxide nanoparticle to form a silica coated magnetic iron oxide nanoparticle. The silica coated magnetic iron oxide nanoparticles were then rinsed with deionized water (40 mL×3), re-suspended in deionized water (40 mL), followed by sonication for 30 min. Aluminum isopropoxide (6 mg) was added to the nanoparticle solution followed by sonication for 30 min at room temperature. The mixture in a reaction vial was reacted at 80° C. in an oil bath with vigorously stirring for 1 h, and then the cap of the vial was opened to remove the generated gas (i.e., 2-propanol). The mixture was reacted at 90° C. for 30 min, followed by the reflux at 90° C. for another 2 h. After the mixture was cooled to room temperature, a metal oxide nano-composite magnetic material were isolated, rinsed with water (40 mL×3), and re-suspended in water before use. FIG. 6 shows the TEM image of the nanoparticles of the metal oxide nano-composite magnetic material.

The Method for Linkage, Enrichment, and Isolation of Phosphorylated Species

α-Casein was prepared in an ammonium bicarbonate solution (0.5 mL, 50 mM) followed by incubation at 38° C. for 30 min. Dithiothreitol (DTT) (50 μL, 100 mM) prepared in ammonium bicarbonate solution (50 mM) was added into this mixture, which was maintained at 50° C. for 1 h. After cooling to room temperature, the sample solution was mixed with iodoacetic acid (IAA) solution (50 μL, 200 mM) prepared in ammonium bicarbonate solution (50 mM) in an ice bath. The sample vial was wrapped with aluminum foil and mixed by vortex mixing for 2.5 h at room temperature. After 2.5 h, the sample solution was ready for carrying out either the enrichment process by the magnetic particles or tryptic digestion. When tryptic digestion was carried out, the denatured α-casein (2 mg/mL, 0.5 mL) obtained above was incubated with trypsin (2 mg/mL, 10 μL) at 37° C. for 18 h. The digestion product was called sample A1.

Figure 7A:
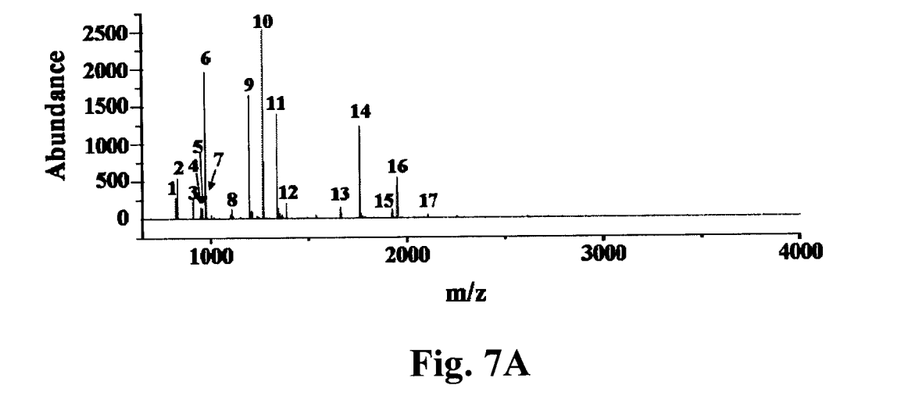
FIG. 7A presents direct MALDI mass spectrum of sample E1 in the present invention's first preferred embodiment.
Figure 7B:
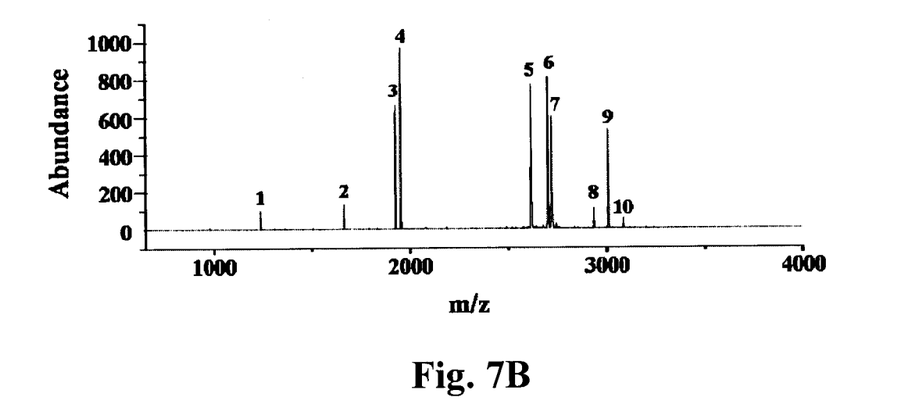
FIG. 7B depicts the MALDI mass spectrum obtained after using aluminum oxide nano-composite magnetic nanoparticles as affinity probes to trap target species from sample E1 of the present invention's first preferred embodiment.
Figure 7C:
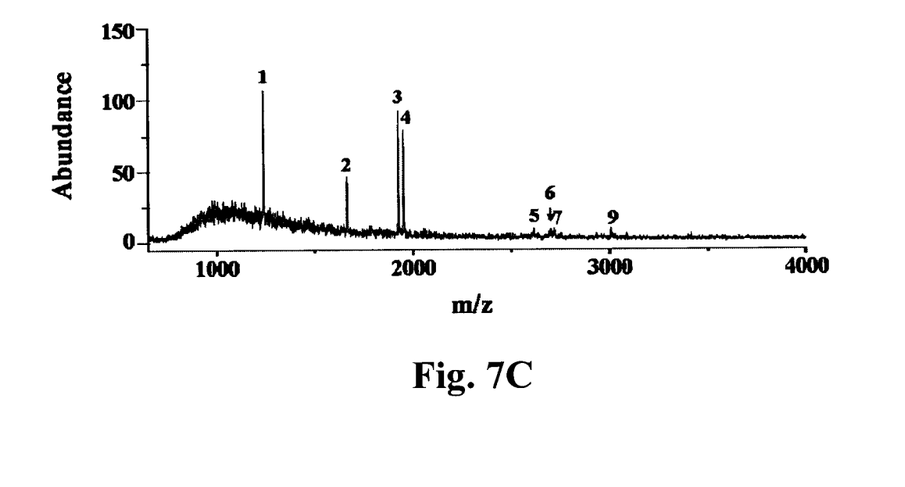
FIG. 7C depicts the MALDI mass spectrum obtained after using aluminum oxide nano-composite magnetic nanoparticles as affinity probes to trap target species from sample E2 of the present invention's first preferred embodiment.

Sample E1 ($10^{-6}$ M) and E2 ($5 \times 10^{-10}$ M) were obtained by diluting sample A1 with aqueous ammonium bicarbonate (50 mM). 2,5-dihydroxy benzoic acid (30 mg/mL) prepared in the mixture of acetonitrile and deionized water (2/1, v/v) containing 1% phosphoric acid was used as the MALDI matrix. FIG. 7A presents the direct MALDI mass spectrum of the tryptic digest product of α-casein ($10^{-5}$ M, 0.3 μL) prior to enrichment. The peaks marked with Arabic numbers correspond to the amino acid sequences for each peptide displayed in Table 1. Only the peaks labeled with 13, 15, and 16 at m/z 1660.57, 1927.66, and 1951.83, respectively, are phosphopeptides. However, after enrichment by using the magnetic particles coated with alumina from sample E1, phosphopeptide residue ions generated from α-casein appear in the MALDI mass spectrum with reasonably good intensities (FIG. 7B and Table 2). There are no ion peaks from non-phosphorylated peptide residues appearing in the mass spectrum. The results indicate that the selectivity of magnetic particles coated with alumina is reasonably good. As the concentration of the sample is lowered down to $5 \times 10^{-10}$ M (sample E2), there are still several phosphorylated peptides marked with numbers 1, 2, 3, 4, 5, 6, 7, and 9 appearing in the mass spectrum (FIG. 7c and Table 2) after enrichment by the particles. The trapping capacity estimated by absorption spectroscopy was 60 μg of phosphopeptides trapped by 1 mg of magnetic nanoparticles.

TABLE 1

Peptide ion peaks observed in the direct MALDI mass spectrum of tryptic digest of α-casein (FIG. 7A)

| No. | Observed [M + H]⁺ | Calculated [M + H]⁺ | Sequences |
|---|---|---|---|
| 1 | 824.40 | 824.43 | YPELFR (S1/146-151) |
| 2 | 831.40 | 831.38 | EDVPSER (S1/84-90) |
| 3 | 910.48 | 910.47 | EGIHAQQK (S1/125-132) |
| 4 | 946.51 | 946.52 | EKVNELSK (S1/35-42) |
| 5 | 958.46 | 958.47 | FPQYLQY (S2/92-98) |
| 6 | 971.54 | 971.50 | FYPELFR (S1/145-151) |
| 7 | 979.62 | 979.56 | FALPQYLK (S2/174-181) |
| 8 | 1107.51 | 1107.51 | QLDAYPSGAW (S1/155-164) |
| 9 | 1195.69 | 1195.08 | NAVPIIPILNR (S2/115-125) |
| 10 | 1267.70 | 1267.70 | YLGYLEQLLR (S1/91-100) |
| 11 | 1337.67 | 1337.68 | HIQKEDVPSER (S1/80-90) |
| 12 | 1384.73 | 1384.73 | FFVAPFPEVFGK (S1/23-34) |
| 13 | 1660.57 | 1660.79 | VPQLEIVPNsAEER (S1/106-119) |
| 14 | 1759.80 | 1759.95 | HQGLPQEVLNENLLR (S1/8-22) |
| 15 | 1927.66 | 1927.69 | DIGsEsTEDQAMEDIK (S1/43-58) |
| 16 | 1951.83 | 1951.95 | YKVPQLEIVPNsAEER (S1/104-119) |
| 17 | 2104.90 | 2104.97 | TDAPSFSDIPNPIGSENSEK (S1/174-193) |

"s" stands for phosphorylated serine.

TABLE 2

Peptide ion peaks observed in the MALDI mass spectrum of sample E1 after enrichment by magnetic nanoparticles coated with alumina (FIG. 7B)

| No. | Observed [M + H]⁺ | Calculated [M + H]⁺ | Sequences |
|---|---|---|---|
| 1 | 1237.33 | 1237.47 | TVDMEsTEVF (S2/138-147) |
| 2 | 1660.73 | 1660.79 | VPQLEIVPNsAEER (S1/106-119) |
| 3 | 1927.69 | 1927.73 | DIGsEsTEDQAMEDIK (S1/43-58) |
| 4 | 1951.93 | 1951.95 | YKVPQLEIVPNsAEER (S1/104-119) |
| 5 | 2618.87 | 2618.90 | NTMEHVsssEESIIsQETYK (S2/2-21) |
| 6 | 2703.62 | 2703.50 | LRLKKYKVPQLEIVPNsAEERL (S1/99-120) |
| 7 | 2720.94 | 2720.91 | QMEAEsIsssEEIVPNsVEQK (S1/59-79) |

TABLE 2-continued

Peptide ion peaks observed in the MALDI mass
spectrum of sample E1 after enrichment by
magnetic nanoparticles coated with alumina
(FIG. 7B)

| No. | Observed $[M + H]^+$ | Calculated $[M + H]^+$ | Sequences |
|---|---|---|---|
| 8 | 2935.29 | 2935.16 | EKVNELsKDIGsEsTEDQAMEDIK (S1/35-58) |
| 9 | 3008.15 | 3008.03 | NANEEEYSIGsssEEsAEVATEEVK (S2/46-70) |
| 10 | 3087.37 | 3087.33 | sTsEENSKKTVDMEsTEVFTKKTL (S2/129-153) |

"s" stands for phosphorylated serine.

Second Preferred Embodiment

Methods for Linkage, Enrichment, and Isolation of Phosphorylated Species

Protein mixtures were prepared in ammonium bicarbonate solution (0.5 mL, 50 mM) containing urea (8 M), while the milk (0.25 mL) was mixed with the same solution (0.25 mL), followed by incubation at 38° C. for 30 min. A DTT (50 µL, 100 mM) prepared in ammonium bicarbonate solution (50 mM) was added into this mixture, which was maintained at 50° C. for 1 h. After cooling to room temperature, the sample solution was mixed with IAA solution (50 µL, 200 mM) prepared in ammonium bicarbonate solution (50 mM) in an ice bath. The sample vial was wrapped with aluminum foil and mixed by vortex mixing for 2.5 h at room temperature. After 2.5 h, the sample solution (sample A2) was ready for carrying out either the enrichment process by the magnetic particles or tryptic digestion.

Figure 8A:
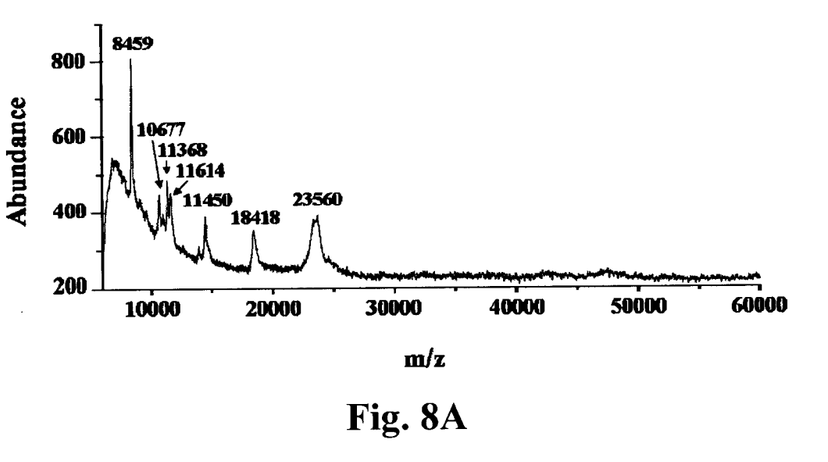
FIG. 8A depicts the direct MALDI mass spectrum of sample A2 of the present invention's second preferred embodiment.
Figure 8B:
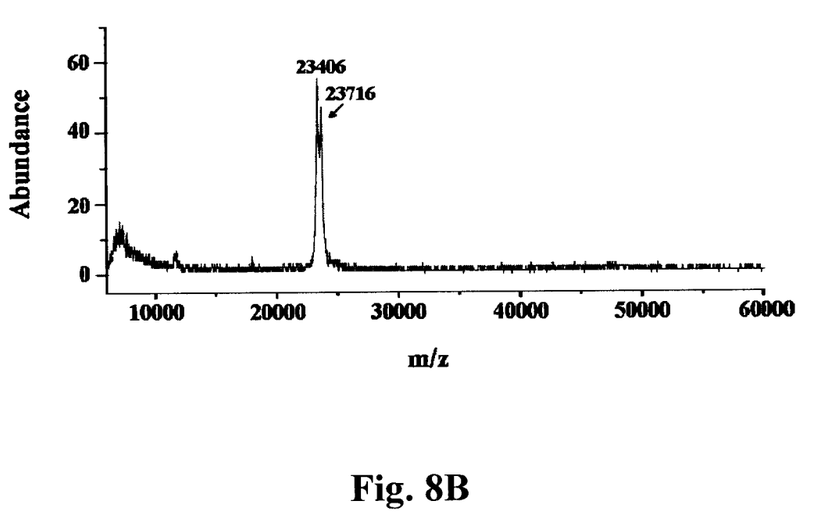
FIG. 8B depicts the MALDI mass spectrum obtained using aluminum oxide nano-composite magnetic nanoparticles as affinity probes to trap target species from sample A2 of the present invention's second preferred embodiment.

To demonstrate the feasibility of employing this approach to a real sample, the nanoparticles of the metal oxide nano-composite magnetic material are used to selectively trap phosphoproteins from a milk sample (sample A2), which commonly contains abundant proteins including phosphoproteins (i.e., α- & β-caseins). Sinapinic acid (30 mg/mL) prepared in an acetonitrile/deionized water (2/1, v/v) solution containing 1% phosphoric acid was used as the MALDI matrix for the analysis of sample A2. FIG. 8A presents the direct MALDI mass spectrum of sample A2. There are several peaks appearing at m/z>8000. To carry out the enrichment of phosphoproteins, sample A2 (5 µL) was mixed with TFA (0.15%, 44.3 µL). Magnetic nanoparticles coated with alumina (40 mg/mL, 0.7 µL) were added to this acidified solution. The mixture was vigorously mixed by pipetting in and out of a sample vial for 90 sec. Magnetic nanoparticles coated with alumina (the metal oxide nano-composite magnetic material) conjugated with their target species were then aggregated on the sample vial wall by positioning a magnet to the outside of the sample vial so that the solution could be easily removed by a pipette. The isolated particles were rinsed with 0.15% TFA solution (60 µL×2) in acetonitrile/deionized water (1/1, v/v), mixing vigorously by pipetting in and out of the mixture in the vial to wash out any unbound impurities. The rinsed particles were mixed with 0.7 µL of sinapinic acid (30 mg/mL), which was prepared in acetonitrile/deionized water (2/1, v/v) solution containing 1% phosphoric acid. After evaporation of the solvent, the sample was ready for MALDI MS analysis. FIG. 8B presents the MALDI mass spectrum obtained using magnetic nanoparticles coated with alumina to trap target species from sample A2. Two unresolved peaks appearing at m/z about 23500 dominate the mass spectrum. The values of m/z resemble those of α- and β-caseins.

Third Preferred Embodiment

Methods for Fabrication of Metal Oxide Nano-Composite Magnetic Nanoparticles $FeCl_3$ (2 g) and $FeCl_2$ (5.4 g) were dissolved in aqueous hydrochloric acid (2 M, 25 mL) at room temperature under sonication. After the salts had dissolved completely in the solution, the mixture was degassed using a vacuum pump and then the flask was filled with nitrogen gas. Aqueous ammonia (25%, 40 mL) was slowly injected into the mixture under nitrogen while stirring at room temperature, followed by rinsing with deionized water three times and re-suspension in ethanol (40 mL). The final concentration of the magnetic iron oxide nanoparticle suspension was 40 mg/mL.

The magnetic iron oxide nanoparticles solution (40 mg/mL, 23 mL) obtained above was sonicated with ethanol (35 mL) and deionized water (6 mL) for 10 min. Tetraethoxysilane (TEOS, 1.5 mL) was added, and the mixture was then sonicated for 10 min; aqueous ammonia (10%, 1.4 mL) was then added slowly over 5 min. The mixture was stirred in a water bath (40° C.) for 12 h. Subsequently, the magnetic iron oxide nanoparticles coated with thin film of silica (silica coated magnetic iron oxide nanoparticle, $Fe_3O_4$@$SiO_2$) in the mixture were rinsed with ethanol and re-suspended in ethanol (40 mL). The concentration of $Fe_3O_4$@$SiO_2$ in the suspension was 14 mg/mL; it was stored at 4° C. in a refrigerator prior to use.

Niobium oxide sol was prepared by stirring niobium ethoxide (0.5 mL) with a mixture of ethanol (3.656 mL) and acetylacetone (2.056 mL) at a mole ratio 1:20:1 for 12 h, followed by the addition of acetic acid (99.8%, 200 µL). The $Fe_3O_4$@$SiO_2$ suspension (14 mg/mL, 1 mL) obtained above was sonicated with ethanol (15 mL) for 30 min and then niobium oxide sol (3 mL) was added. The mixture was stirred in a water bath at 70° C. for 6 h. The generated $Fe_3O_4$@$Nb_2O_5$ nanoparticles ($Nb_2O_5$ coated onto the surface of the silica coated magnetic iron oxide nanoparticle) were rinsed several times with ethanol and deionized water, then they were re-suspended in deionized water. The concentration of $Fe_3O_4$@$Nb_2O_5$ nanoparticles in the suspension was 0.74 mg/mL; it was stored at 4° C. in a refrigerator prior to use.

Methods for Linkage, Enrichment, and Isolation of Phosphorylated Species

Samples E3 ($4\times10^{-7}$ M), E4 ($4\times10^{-8}$ M), E5 ($4\times10^{-9}$ M), and E6 ($10^{-9}$ M) were obtained by diluting sample A1 with aqueous ammonium bicarbonate aqueous solution (50 mM) followed by 10-fold dilution with 0.15% TFA. Niobium oxide-coated magnetic nanoparticles ($Fe_3O_4$@$Nb_2O_5$ nanoparticle) (12 µg) isolated from the suspension solution were added to E3~E6 (50 µL). To perform an enrichment experiment, the mixture was placed in a domestic microwave oven and was heated for 1 min (900 W). The $Fe_3O_4$@$Nb_2O_5$ nanoparticles (the metal oxide nano-composite magnetic material of this invention) conjugated to their target species were then aggregated on the vial wall by positioning a magnet on the outside of the sample vial so that the solution could be easily removed using a pipette. The isolated nanoparticles were rinsed with 0.15% TFA solution (3×160 µL) in acetonitrile/deionized water (1:1, v/v), mixing vigorously each time with a pipette to wash out any unbound impurities. The rinsed nanoparticles were mixed with 2,5-DHB solution (30 mg/mL, 0.8 μL) prepared in acetonitrile/deionized water (2:1, v/v) containing 0.5% phosphoric acid. The mixture was deposited on a MALDI sample plate. After evaporation of the solvent, the sample was ready for MALDI MS analysis.

Figure 9A:
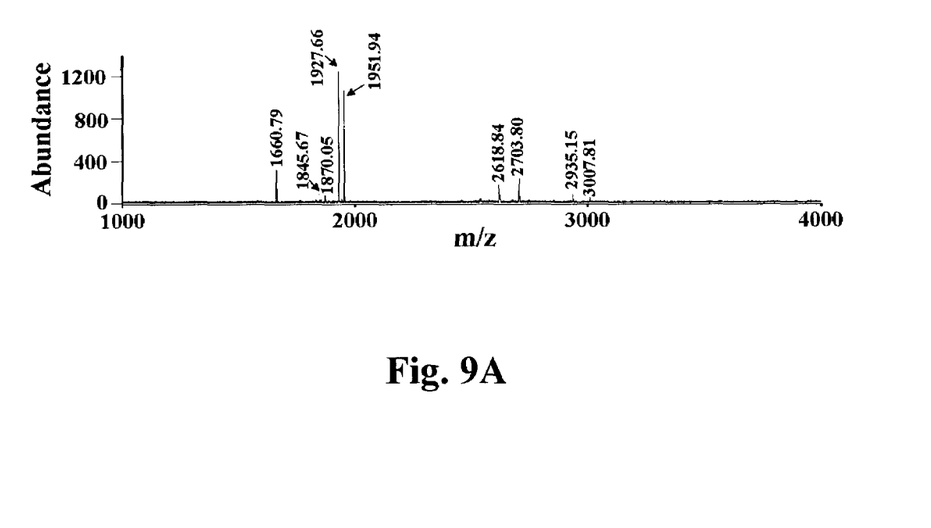
FIG. 9A depicts the MALDI mass spectrum obtained using niobium oxide nano-composite magnetic nanoparticles as affinity probes to trap target species from sample E3 of the present invention's third preferred embodiment.
Figure 9B:
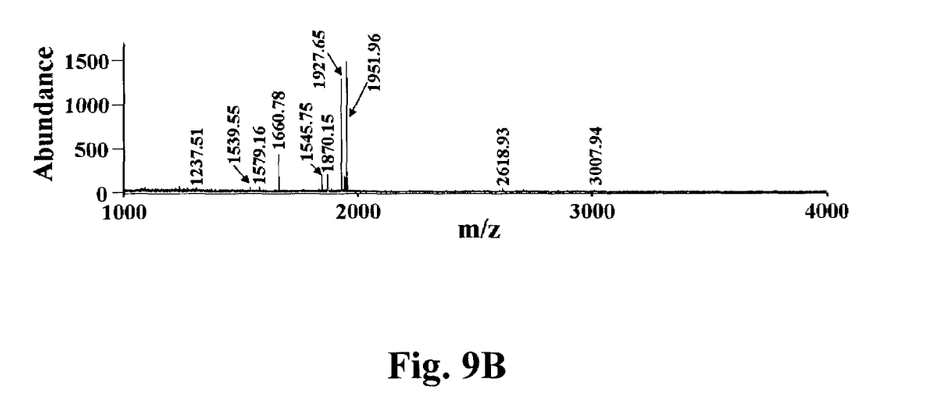
FIG. 9B depicts the MALDI mass spectrum obtained after using niobium oxide nano-composite magnetic nanoparticles as affinity probes to trap target species from sample E4 of the present invention's third preferred embodiment.
Figure 9C:
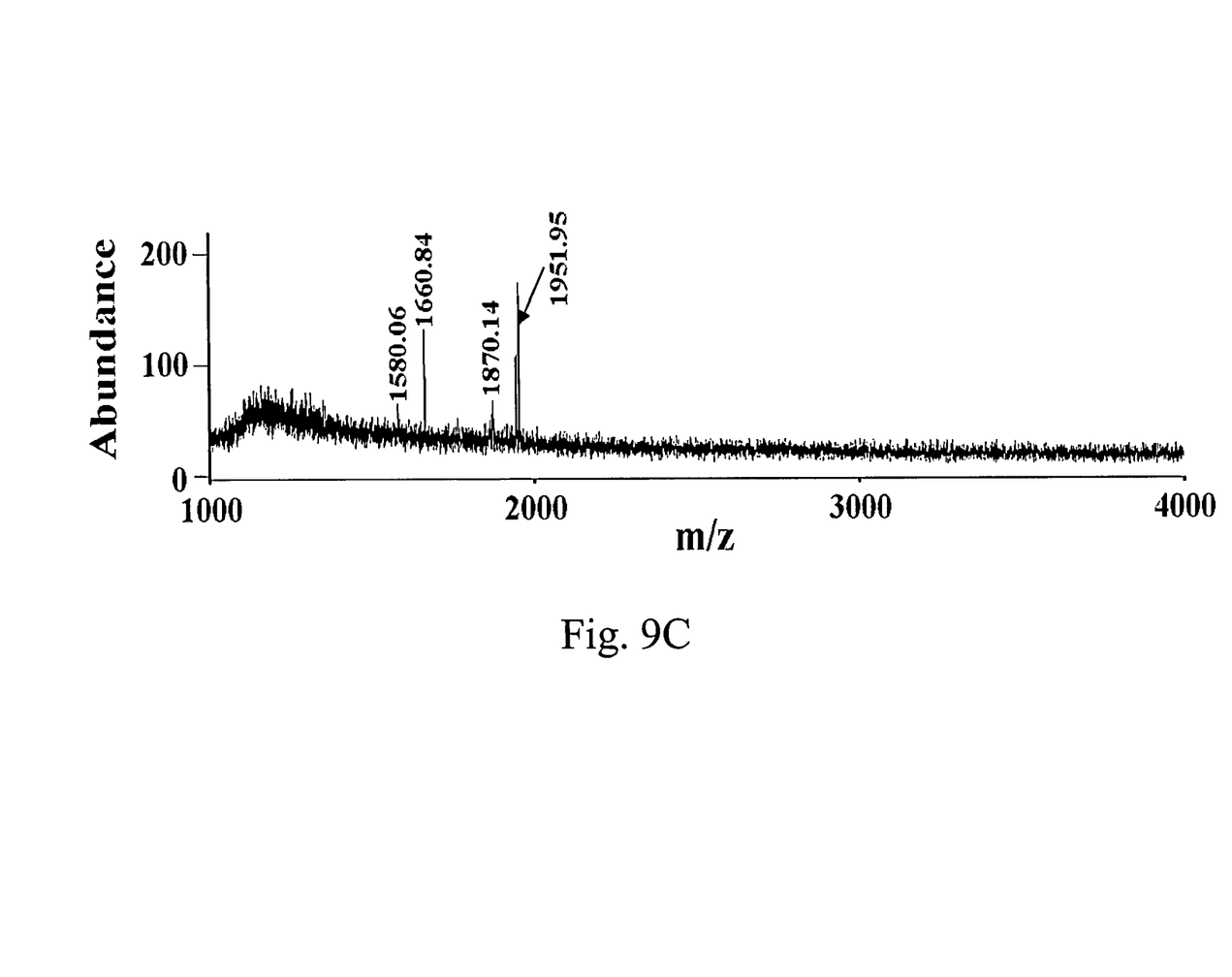
FIG. 9C depicts the MALDI mass spectrum obtained using niobium oxide nano-composite magnetic nanoparticles as affinity probes to trap target species from sample E5 of the present invention's third preferred embodiment.
Figure 9D:
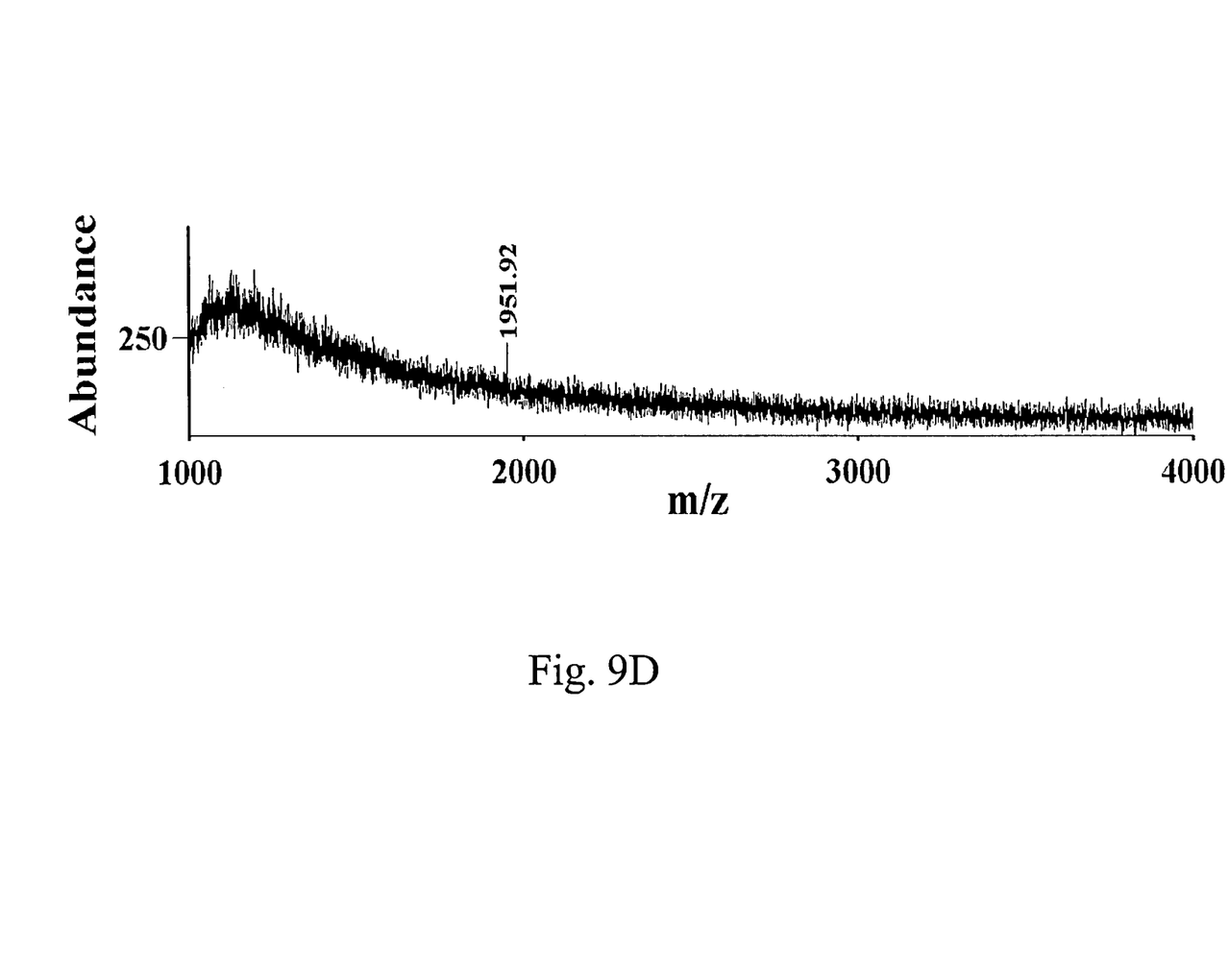
FIG. 9D depicts the MALDI mass spectrum obtained after using niobium oxide nano-composite magnetic nanoparticles as affinity probes to trap target species from sample E6 of the present invention's third preferred embodiment.

FIGS. 9A and 9B present the MALDI mass spectra of the samples obtained when using $Fe_3O_4@Nb_2O_5$ magnetic nanoparticles as affinity probes to trap phosphopeptides from samples E3 and E4, respectively. The peaks at m/z 1237.51, 1539.55, 1660.79, 1927.66, 1951.94, 2618.84, 2703.80, 2935.15, and 3007.81 are derived from phosphopeptides, while the peaks at m/z 1845.67 and 1870.05 are the fragments of the peaks at m/z 1927.66 and 1951.94 by the loss of a $HPO_3^-$. Table 3 lists the corresponding peptide sequences of the peaks appearing in FIGS. 9A-9D. When the concentration of the digest was lowered by one order, only the peaks at m/z 1580.06, 1660.84, and 1951.95 derived from phosphopeptides appear in the mass spectrum (FIG. 9C). The peak at m/z 1870.14 is the fragment of the peak at m/z 1951.95 by losing $HPO_3^-$. FIG. 9D shows the MALDI mass spectrum of E6 obtained after enrichment by $Fe_3O_4@N_2O_5$ nanoparticles. Only one peak at m/z 1951.92 is observed.

TABLE 3

Peptide ion peaks observed in the MALDI mass spectra of FIGS. 9A-9D

| Observed (m/z) | Calculated (m/z) | Sequences |
|---|---|---|
| 1237.51 | 1237.47 | TVDMEsTEVF (S2/138-147) |
| 1539.55 | 1539.60 | EQLsTsEENSKK (S2/126-137) |
| 1660.79 | 1660.79 | VPQLEIVPNsAERR (S1/106-119) |
| 1927.66 | 1927.69 | DIGsEsTEDQAMEDIK (S1/43-58) |
| 1951.94 | 1951.95 | YKVPQLEIVPNsAERR (S1/104-119) |
| 2618.84 | 2618.90 | NTMEHVsssEESIIsQETYK (S2/2-21) |
| 2703.80 | 2703.50 | LRLKKYKVPQLEIVPNsAEERL (S1/99-120) |
| 2935.15 | 2935.16 | EKVNELsKDIGsEsTEDQAMEDIK (S1/35-58) |
| 3007.81 | 3008.03 | NANEEEYSIGsssEEsAEVATEEVK (S2/46-70) |

"s" stands for phosphorylated serine

The present invention aims to demonstrate the methods for fabrication of metal oxide nano-composite magnetic materials and their use for the linkage, enrichment, and isolation of phosphorylated species from complex samples. On the basis of magnetic property, affinity with phosphorylated species, and the capability of absorbing microwave radiation, the metal oxide nano-composite magnetic nanoparticles presented in the current invention have multi-functions. As a consequence, the nanoparticles can be effectively used for either linking or enriching phosphorylated species such as phosphoproteins and phosphopeptides from complex samples with high specificity under microwave heating within 30~90 sec. The time required to carry out the whole process is extremely short compared to that has ever been reported. Thus, the advantages of the present invention include small-sample consumption, high specificity, high sensitivity, high extraction efficiency, ease of operation, and short analysis time. While certain preferred embodiments of the present invention have been disclosed in details, it is to be understood that various modifications such as using different metal oxides for fabrication of the shell of magnetic nanoparticles may be adopted without departing from the spirit of the invention or the scope of the following claims.

We claim:

1. A metal oxide nano-composite magnetic material comprising:
    a magnetic iron oxide nanoparticle;
    a silica layer immobilized onto the surface of the magnetic iron oxide nanoparticle; and
    a zinc oxide layer coated onto the surface of the silica layer.

* * * * *